US011110005B2

(12) United States Patent
Diao et al.

(10) Patent No.: US 11,110,005 B2
(45) Date of Patent: Sep. 7, 2021

(54) MEDICAL INSTRUMENT WITH AN INTEGRATED OPTICAL FIBER

(71) Applicant: Novartis AG, Basel (CH)

(72) Inventors: Chenguang Diao, Irvine, CA (US); Mark Harrison Farley, Laguna Hills, CA (US); Brian William McDonell, Irvine, CA (US); Alireza Mirsepassi, Irvine, CA (US); Michael J. Papac, North Tustin, CA (US); Kambiz Parto, Laguna Niguel, CA (US); Ronald T. Smith, Irvine, CA (US); Barry L. Wheatley, Oceanside, CA (US)

(73) Assignee: Alcon Inc., Fribourg (CH)

( * ) Notice: Subject to any disclaimer, the term of this patent is extended or adjusted under 35 U.S.C. 154(b) by 666 days.

(21) Appl. No.: 15/814,929

(22) Filed: Nov. 16, 2017

(65) Prior Publication Data

US 2018/0133057 A1    May 17, 2018

Related U.S. Application Data

(60) Provisional application No. 62/543,548, filed on Aug. 10, 2017, provisional application No. 62/423,499, filed on Nov. 17, 2016.

(51) Int. Cl.
*A61F 9/00* (2006.01)
*A61F 9/008* (2006.01)
*A61F 9/009* (2006.01)
*A61F 9/007* (2006.01)
*A61B 3/00* (2006.01)
*A61B 90/30* (2016.01)
*A61B 90/00* (2016.01)

(52) U.S. Cl.
CPC .......... *A61F 9/00802* (2013.01); *A61F 9/009* (2013.01); *A61F 9/00754* (2013.01); *A61F 9/00763* (2013.01); *A61B 3/0025* (2013.01); *A61B 2090/306* (2016.02); *A61B 2090/3735* (2016.02); *A61F 9/007* (2013.01); *A61F 9/0008* (2013.01); *A61F 9/00745* (2013.01)

(58) Field of Classification Search
CPC combination set(s) only.
See application file for complete search history.

(56) References Cited

U.S. PATENT DOCUMENTS 5,201,730 A    4/1993  Easley
5,275,593 A    1/1994  Easley et al.
(Continued)

*Primary Examiner* — Shirley X Jian

(57) ABSTRACT

In some embodiments, an illuminated microsurgical instrument system includes a microsurgical instrument having a distally projecting tubular member arranged to perform a medical procedure. The tubular member has a distal tip and an outer surface, the outer surface having a flat surface formed therein. The instrument includes a sheath member surrounding a portion of the tubular member and extending toward the distal tip of the tubular member and an optical fiber extending along a length of the flat surface between the tubular member and the sheath member. The instrument may include an opening such as a slot in the distal end of the sheath member to direct exiting air away from the tip of the optical fiber. The instrument may further include a slack chamber, collar structure, and fiber guard member to support and guide the optical fiber to the distal tip.

20 Claims, 13 Drawing Sheets

(56) References Cited

U.S. PATENT DOCUMENTS

| | | |
|---|---|---|
| 5,591,160 A | 1/1997 | Reynard |
| 5,651,783 A | 7/1997 | Raynard |
| 5,916,149 A | 6/1999 | Ryan, Jr. |
| 7,783,346 B2 | 8/2010 | Smith et al. |
| 8,968,347 B2 | 3/2015 | McCollam |
| 9,055,885 B2 | 6/2015 | Horvath |
| 9,089,364 B2 | 7/2015 | Bhadri |
| 9,364,982 B2 | 6/2016 | Schaller |
| 9,402,643 B2 | 8/2016 | Auld |
| 9,510,847 B2 | 12/2016 | Auld |
| 9,561,085 B2 | 2/2017 | Yadlowsky |
| 9,839,749 B2 | 12/2017 | Johnson |
| 9,956,053 B2 | 5/2018 | Diao |
| 10,016,248 B2 | 7/2018 | Mirsepassi |
| 10,022,200 B2 | 7/2018 | Richmond |
| 10,039,669 B2 | 8/2018 | Heeren |
| 10,244,931 B2 | 4/2019 | Kern |
| 10,307,290 B2 | 6/2019 | Kern |
| 10,322,028 B2 | 6/2019 | Price |
| 10,376,414 B2 | 8/2019 | Hallen |
| 10,485,630 B2 | 11/2019 | Dos Santos |
| 10,869,735 B2 * | 12/2020 | Diao ................... A61F 9/00736 |
| 2009/0161384 A1 | 6/2009 | Smith |
| 2010/0004642 A1 * | 1/2010 | Lumpkin ................. A61F 9/008 606/4 |
| 2012/0283523 A1 * | 11/2012 | Yadlowsky ........ G02B 23/2469 600/249 |
| 2014/0121469 A1 | 5/2014 | Meckel |
| 2016/0113722 A1 * | 4/2016 | Heeren .................. A61B 90/30 600/249 |
| 2017/0014023 A1 | 1/2017 | Kern |
| 2017/0014267 A1 | 1/2017 | Kern |
| 2017/0119491 A1 | 5/2017 | Mirsepassi |
| 2017/0165114 A1 | 6/2017 | Hallen |
| 2018/0055596 A1 | 3/2018 | Johnson |
| 2018/0132963 A1 | 5/2018 | Diao |
| 2018/0133057 A1 | 5/2018 | Diao |
| 2018/0168768 A1 | 6/2018 | Mirsepassi |
| 2018/0168861 A1 | 6/2018 | Mirsepassi |
| 2018/0338776 A1 | 11/2018 | Farley |
| 2018/0338859 A1 | 11/2018 | Mirsepassi |
| 2018/0338860 A1 | 11/2018 | Farley |
| 2019/0209372 A1 | 7/2019 | Farley |
| 2019/0282322 A1 | 9/2019 | Mirsepassi |

* cited by examiner

MEDICAL INSTRUMENT WITH AN INTEGRATED OPTICAL FIBER

This application claims the benefit of priority of U.S. Provisional Patent Application Ser. No. 62/543,548 titled "Medical Instrument with an Integrated Optical Fiber", filed on Aug. 10, 2017, whose inventors are Chenguang Diao, Mark Harrison Farley, Brian William McDonell, Alireza Mirsepassi, Michael J. Papac, Kambiz Parto, Ronald T. Smith, and Barry L. Wheatley, which is hereby incorporated by reference in its entirety as though fully and completely set forth herein.

This application also claims the benefit of priority of U.S. Provisional Patent Application Ser. No. 62/423,499 titled "Medical Instrument with an Integrated Optical Fiber", filed on Nov. 17, 2016, whose inventors are Chenguang Diao, Mark Harrison Farley, Brian William McDonell, Alireza Mirsepassi, Michael J. Papac, Kambiz Parto, Ronald T. Smith, and Barry L. Wheatley, which is hereby incorporated by reference in its entirety as though fully and completely set forth herein.

TECHNICAL FIELD

The present disclosure is directed to systems and instruments for use in medical procedures, and more particularly, to methods and systems involving a need for an optical fiber to be inserted within a body cavity.

BACKGROUND

Medical procedures are often performed within significantly limited confines of a particular body structure or cavity, such as within the posterior chamber of the human eye. For example, vitreo-retinal procedures are commonly performed to treat many serious conditions of the posterior segment of the eye. In particular, vitreo-retinal procedures may treat conditions such as age-related macular degeneration (AMD), diabetic retinopathy and diabetic vitreous hemorrhage, macular hole, retinal detachment, epiretinal membrane, cytomegalovirus (CMV) retinitis, and many other ophthalmic conditions.

A surgeon performs vitreo-retinal procedures with a microscope and special lenses designed to provide a clear image of the posterior segment. Several tiny incisions just a millimeter (mm) or so in diameter are made on the sclera at the pars plana. The surgeon inserts microsurgical instruments through the incisions, such as a light source to illuminate inside the eye, an infusion line to maintain the eye's shape during surgery, and other instruments to cut and remove the vitreous body. A separate incision may be provided for each microsurgical instrument when using multiple instruments simultaneously.

During such procedures, proper illumination of the inside of the eye is important. Typically, an optical fiber is inserted into one of the incisions in the eye to provide the illumination. A light source, such as a halogen tungsten lamp or high pressure arc lamp (metal-halides, Xenon), may be used to produce the light carried by the optical fiber into the eye. The light passes through several optical elements (typically lenses, mirrors, and attenuators) and is transmitted to the optical fiber that carries the light into the eye.

In such procedures, incisions are typically only made large enough to accommodate the size of the microsurgical instrument being inserted into the interior of the eye. Efforts to minimize the incision size generally involve reducing the size of the microsurgical instrument. However, a reduction in size can result in a reduction in instrument strength or rigidity. Depending on the size of the microsurgical instrument employed, the incision may be small enough to render a resulting wound substantially self-healing, thereby eliminating the need to employ additional procedures to close the incision, such as sutures. Also, reducing the number of incisions may be accomplished by integrating various microsurgical instruments. For example, the optical fiber may be incorporated into the working end of a microsurgical instrument. Unfortunately, at least some prior attempts at integrating optical fibers with microsurgical instruments have resulted in a decrease in illuminating efficiency or in other visualization problems that otherwise adversely effected the distribution of light emitted from the optical fibers.

SUMMARY

The present disclosure is directed to exemplary illuminated microsurgical instruments.

Exemplary surgical systems are provided herein. One general aspect includes an illuminated microsurgical instrument system that may include a microsurgical instrument having a distally projecting tubular member arranged to perform a medical procedure at an interventional site. The tubular member may have a distal tip and an outer surface, the outer surface having a flat surface formed therein. The instrument may include a sheath member surrounding a portion of the tubular member and extending toward the distal tip of the tubular member and an optical fiber extending along a length of the flat surface between the tubular member and the sheath member.

Another general aspect includes another illuminated microsurgical instrument system. The system may include a microsurgical instrument having a tubular member arranged to perform a medical procedure at an interventional site, the tubular member may have a distal tip and an outer cylindrical surface. The instrument may include a sheath member surrounding a portion of the tubular member and extending toward the distal tip of the tubular member and an optical fiber extending along a length of the tubular member between the outer cylindrical surface and an inner surface of the sheath member. The tip of the optical fiber may be recessed or set back proximally from a distal edge of the tubular member.

Exemplary vitrectomy probes are provided herein. One general aspect includes an illuminated medical probe, which may include a handpiece housing configured to be held in a human hand. The handpiece housing may include a distal end arranged to receive an optical fiber coupled to an illumination source and a proximal end coupled to an elongate tubular member. The illuminated medical probe may also include an optical fiber slack chamber disposed between the distal end and the proximal end. Additionally, the illuminated medical probe may have an optical fiber extending within the optical fiber slack chamber and extending along a portion of the elongate tubular member. A distal region of the optical fiber may be secured at a distal end thereof to the elongate tubular member. The optical fiber may have a slack portion including a bend disposed within the optical fiber slack chamber.

An illuminated microsurgical instrument system or illuminated medical probe as described herein may include a sheath member surrounding a portion of the tubular member, with an optical fiber extending along a length of the tubular member between the outer surface of the tubular member and an inner surface of the sheath member, wherein the sheath member has an opening in its sidewall at or near its distal end. The opening may be in the form of a slot extending proximally from a distal edge of the sheath member. The opening or slot may be located adjacent to an air gap between the tubular member and the sheath member, proximal to a distal edge of the sheath member, and circumferentially away from the tip of the optical fiber. The opening or slot is adapted to direct air exiting the air gap away from the tip of the optical fiber.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the accompanying drawings and the following detailed description.

BRIEF DESCRIPTION OF THE DRAWINGS

The accompanying drawings illustrate implementations of the devices and methods disclosed herein and together with the description, serve to explain the principles of the present disclosure.

Figure 1:
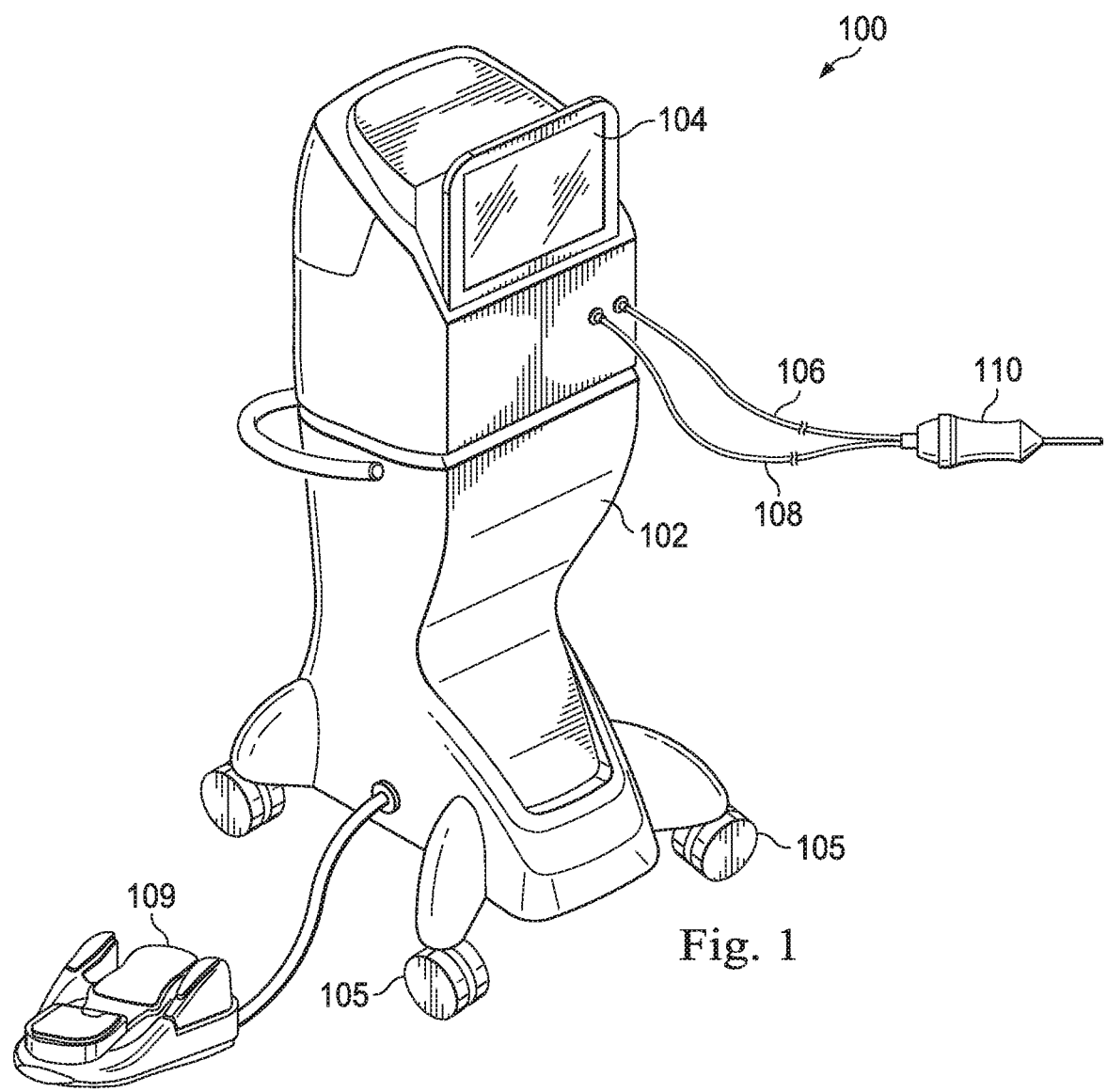
FIG. 1 illustrates a perspective view of an exemplary surgical system, according to an implementation consistent with the principles of the present disclosure.

The accompanying drawings may be better understood by reference to the following detailed description.

DETAILED DESCRIPTION

For the purposes of promoting an understanding of the principles of the present disclosure, reference will now be made to the implementations illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one implementation may be combined with the features, components, and/or steps described with respect to other implementations of the present disclosure. For simplicity, in some instances the same reference numbers are used throughout the drawings to refer to the same or like parts.

The present disclosure is broadly directed to systems and instruments for providing an optical fiber within a body cavity during an operation performed therein without requiring a separate incision to be made. More particularly, some aspects of the present disclosure are directed to systems and instruments for providing for illumination through an optical fiber positioned within the body cavity. In some examples, the illumination is provided through an optical fiber extending along a length of another surgical instrument or tool within the body cavity. For example, a vitrectomy procedure may be performed to remove vitreous from the eye of a patient using a vitrectomy probe introduced into the eye to position a vitrectomy needle at an interventional site. Rather than form two incisions in the eye of the patient, the optical fiber may be positioned along a portion of the vitrectomy needle. The optical fiber may have a distal tip through which light is introduced or emitted into the posterior chamber of the eye, when the distal tip of the vitrectomy probe is positioned within the eye. The removal of the vitreous may be of particular importance, because residual vitreous can cause post-operative retinal tearing, retinal detachment, etc.

The clear vitreous may be visualized due to light scattering off the vitreous fibers contained within it. The lighting may be directed proximate the cutting portion of the vitrectomy probe in order to better visualize the vitreous being cut. Depending on the implementation, the optical fiber may be secured at least partially to a vitrectomy needle by a sheath that also protects the optical fiber. Thus, implementations of the present disclosure provide for improved illumination for inner-cavity procedures, such as vitrectomy procedures, while minimizing the number of incisions required to be made to permit entry to the cavity. The illumination provided by implementations of the present disclosure may result in high irradiance at the surgical site, e.g., at the port of the vitrectomy needle. This may provide for a high signal to noise ratio or contrast to facilitate visualization of the fibers in the vitreous. While specific examples of implementations are provided herein that are directed to vitrectomy procedures and devices, the principles of the present disclosure extend beyond vitrectomy instruments and procedures.

FIG. 1 illustrates a surgical system 100, according to an exemplary implementation. The surgical system 100 includes a base housing or console 102 and an associated display screen 104. In the implementations of the surgical system 100 that are directed to vitrectomy procedures, the display screen 104 may show data relating to system operation and performance during such vitrectomy surgical procedures. In an implementation, the console 102 may be mobile, for example including casters or wheels 105 to facilitate movement as necessary. In an alternative implementation, the console 102 may not include wheels 105.

The console 102 may be referred to as a "base housing" and may include a plurality of subsystems that cooperate to enable a surgeon to perform a variety of medical procedures, such as ophthalmic surgical procedures. A microsurgical, or simply "surgical," instrument 110, which may be implemented as a handpiece, may attach to the console 102 and may form a part of the surgical system 100. The surgical instrument 110 may be a vitrectomy probe, in some implementations. Additionally, some implementations of the instrument 110 may include non-surgical medical instruments, such as diagnostic instruments, imaging instruments, or therapeutic instruments. As illustrated in FIG. 1, the surgical instrument 110 is an illuminated vitrectomy probe that may form part of a vitrectomy subsystem as described herein. The vitrectomy probe may include an outer vitrectomy needle and an inner reciprocating cutter.

The surgical instrument 110 may be coupled to the console 102 by one or more conduits. In the depicted implementation, the surgical instrument 110 is coupled to the console 102 by a first conduit 106 and a second conduit 108. The conduits 106 and 108 may provide the surgical instrument 110 with access to multiple subsystems of the console 102. For example, the first conduit 106 may contain an optical fiber coupled to or forming part of a fiber subsystem within the console 102, while the second conduit 108 may couple the surgical instrument 110 to or may form a part of a fluidics subsystem.

To facilitate operator control of the surgical system 100, the surgical instrument 110 itself may include one or more control elements, such as buttons or dials. Additionally, a footpedal 109 may include control elements that can be activated, deactivated, or varied by the operator's foot. Moreover, the display screen 104 may be a touchscreen having controls displayed thereon that can be manually activated by the operator. Other mechanisms such as voice control, a keyboard, a mouse, etc., may be provided in various implementations of the surgical system 100 to facilitate control of various subsystems, such as a fiber subsystem to facilitate visualization, diagnosis, or treatment at a distal region of the surgical instrument 110.

Figure 2:
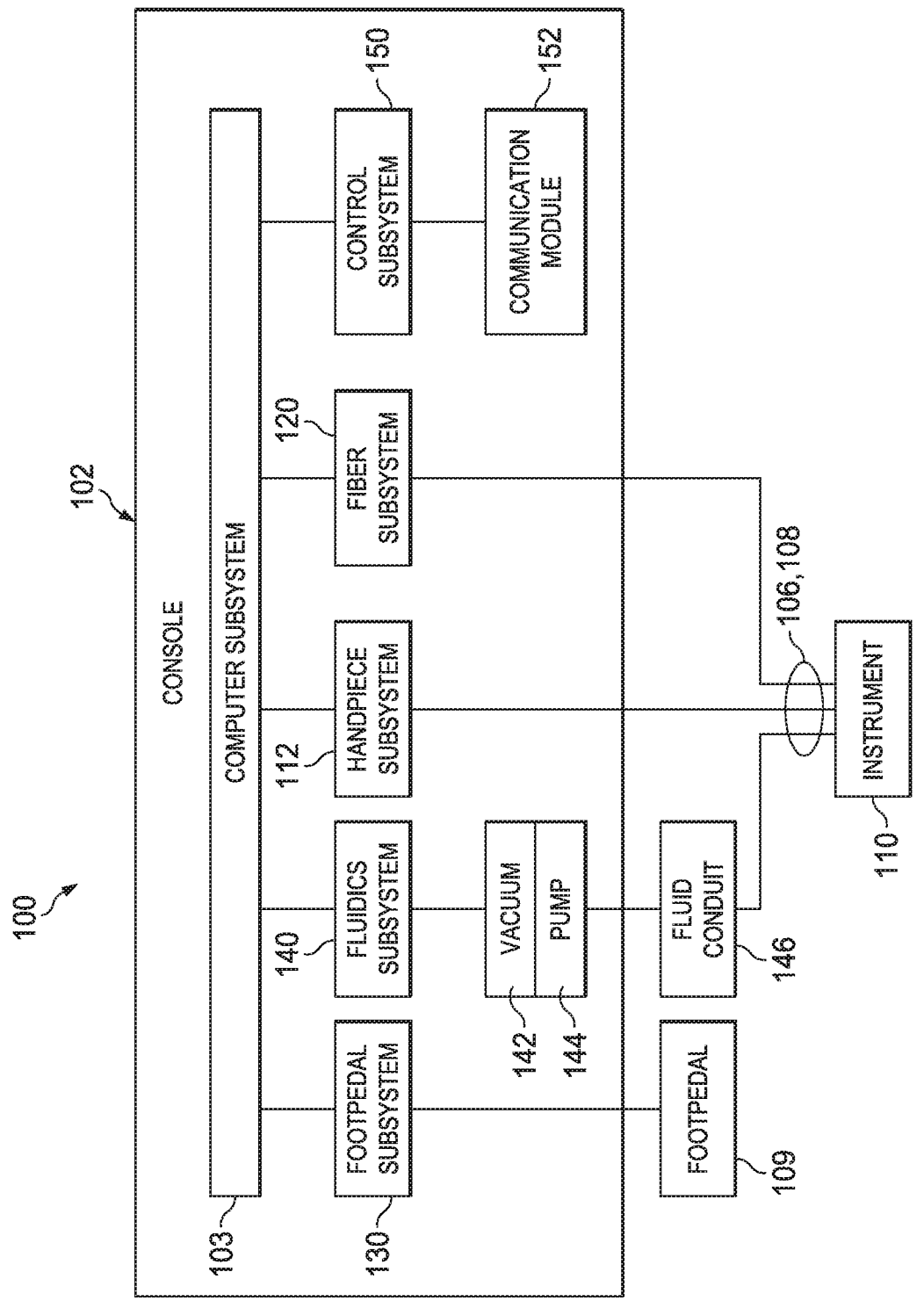
FIG. 2 is an illustration of an exemplary block diagram of the surgical system of FIG. 1, according to an aspect consistent with the principles of the present disclosure.

FIG. 2 is a block diagram of the surgical system 100 including the console 102 and several relating subsystems thereof. As illustrated, console 102 includes a computer subsystem 103, the display screen 104 (FIG. 1), and a number of subsystems that are used together to perform ocular surgical procedures, such as emulsification or vitrectomy surgical procedures, for example. The computer subsystem 103 may include one or more processing devices, such as a central processing unit or central processor, and an information or data storage system. The data storage system may include one or more types of memory, such as RAM (Random-access memory), ROM (read-only memory), flash memory, a disk-based hard drive, and/or a solid-state hard drive. The processing devices and storage system may communicate over a bus, which may also permit communication with and between one or more of the plurality of subsystems of the surgical system 100.

The subsystems in the exemplary implementation of FIG. 2 may include a footpedal subsystem 130, for example, for facilitating control via the footpedal 109 of FIG. 1. The depicted surgical system 100 further includes a fluidics subsystem 140, which may include an aspiration vacuum 142 and an irrigation pump 144 that connect to a fluid conduit 146. The surgical system 100 includes a handpiece subsystem 112 to facilitate operation and control of the surgical instrument 110. For example, the handpiece subsystem 112 may receive control signals from the surgical instrument 110 to turn on or off an illumination source coupled to the surgical instrument 110.

Implementations of an included fiber subsystem 120 may provide an illumination source. Other implementations of the fiber subsystem 120 may provide laser light for ablation, may be used in imaging through the optical fiber, or other functions. The fiber subsystem 120, which may be an illumination subsystem, may be coupled to the surgical instrument 110 by an optical fiber, extending within one of the first and second conduits 106 and 108. The fiber subsystem 120 may include or be referred to as an illumination source or light source, although the source may be one component of several components of the fiber subsystem 120. Implementations of the fiber subsystem 120 may further include sensors, lenses, filters, and other optical devices.

The surgical system 100 further includes a control subsystem 150 including a communication module 152. The control subsystem 150 may facilitate communication between the subsystems included in the surgical system 100. For example, an operator may provide an input via the footpedal 109. The input may be interpreted or encoded by the footpedal subsystem 130 as a control signal to vary, for example, an intensity of illumination provided to the surgical instrument 110. The footpedal subsystem 130 may communicate the control signal to the control subsystem 150, which may interact with a fiber subsystem 120 to alter a characteristic of illumination provided by the subsystem 120 or to turn the illumination on or off. In some implementations, the surgical instrument 110 may, additionally or alternatively, be used to control illumination status or intensity. For example, the surgical instrument 110 may include a dimmer switch or other control mechanism to receive input from an operator to adjust the illumination.

These subsystems and others may be included additionally or alternatively in other implementations. To optimize performance of the different subsystems during surgery, the operating parameters differ according to, for example, the particular procedure being performed, the different stages of the procedure, the surgeon's personal preferences, whether the procedure is being performed in the anterior or posterior portion of the patient's eye, and so on.

The different subsystems in the console 102 comprise control circuits for the operation and control of the respective microsurgical instruments or instrument components. The computer subsystem 103 and the control subsystem 150 may govern and dynamically redefine the interactions and relationships between the different subsystems to properly perform an ocular surgical procedure and to properly communicate information to the operator of the surgical system 100 through the display 104 and/or through a coupled microscope or wearable computing device.

As shown in FIG. 2, the surgical instrument 110 may be coupled to various subsystems within the surgical system 100. As depicted, the surgical instrument 110 is connected to the handpiece subsystem 112, the fiber subsystem 120, and the fluidic subsystem 140 via the conduits 106 and/or 108 as shown in FIG. 1.

Using the input devices, a surgeon, scientist, or other user may select or adjust parameters that affect the relationships between the different subsystems of the console 102 and that affect the performance of the surgical instrument 110 and/or additional instruments connected to the console 102. For example, a surgeon may increase or decrease an intensity of light provided by the fiber subsystem 120. Additionally, a surgeon may change one or more parameters for the operation of the surgical instrument 110, such as an aspiration/suction parameter or an oscillation parameter of the vitreous cutting mechanism included in the surgical instrument 110. Accordingly, based on a user input, a user may change or adjust the relationships from those that were coded into the console by the system programmers.

Because the surgical instrument 110 is configured to receive light from the fiber subsystem 120, the surgeon may be able to visualize aspects of the surgical operations performed by or near by the distal tip of the surgical instrument 110, without requiring multiple incisions and without requiring the manipulation and handling of two or more separate devices within the small confines of the eye or in another cavity or area of the patient.

Figure 3:
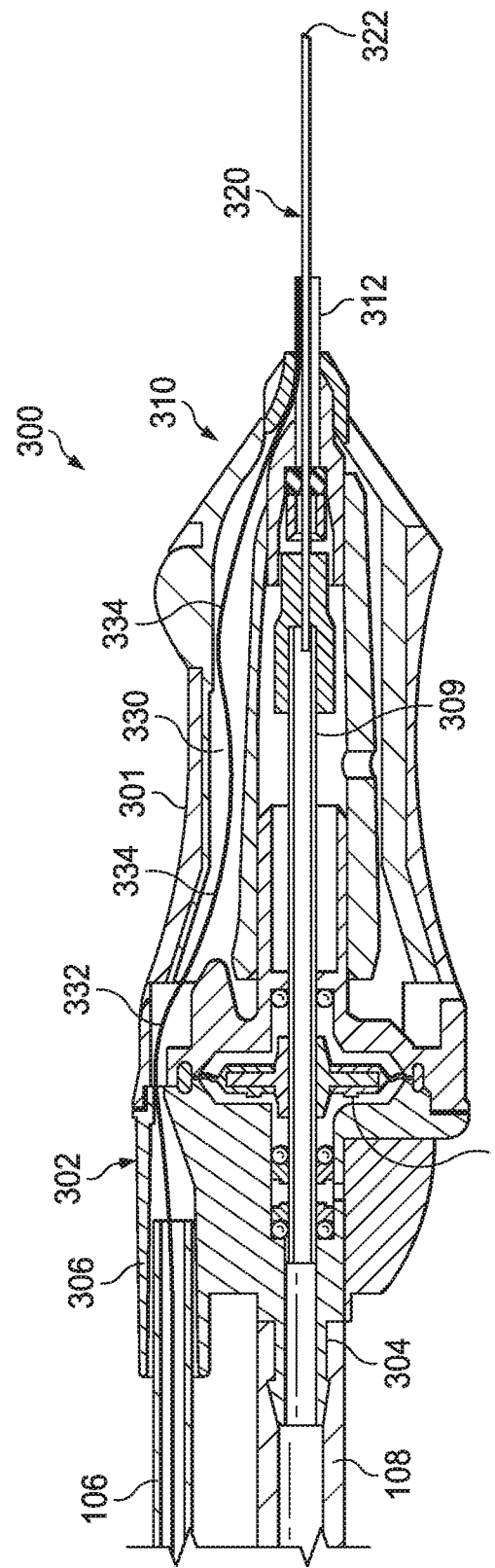
FIG. 3 is a cross-sectional illustration of an exemplary surgical instrument, according to aspects of the present disclosure.

FIG. 3 shows a partial cross-sectional illustration of an exemplary vitrectomy probe 300 that may correspond to the surgical instrument 110 shown in FIGS. 1 and 2. In this example, the probe 300 may be a pneumatically-driven vitrectomy probe configured to be held in the hand of a surgeon during use. The probe 300 includes a handpiece housing 301 having a proximal end 302 and a distal end 310. Some implementations of the probe 300 operate by receiving pneumatic pressure via the second conduit 108 of FIG. 1, which may be coupled to a protruding coupler 304 at the proximal end 302. The coupler 304 may attach the proximal end 302 of the probe 300 to the second conduit 108 by a barb, an adhesive, or other coupling means. The proximal end 302 further includes an additional coupler 306 that is configured to receive or couple to the first conduit 106 of FIG. 1.

In this implementation, the second conduit 108 provides an activation energy source to provide an oscillation energy to components of the probe 300. As illustrated, a pneumatic source may form a part of the fluidics subsystem 140 of FIG. 2 and may be coupled to an oscillation motor, shown here as a diaphragm 308. In some embodiments, the oscillation motion may be provided by an oscillating electric motor or other non-pneumatic activation means. Further, the conduit 108 may be coupled to an aspiration source to enable aspiration of material through the probe 300. By causing the diaphragm 308 to oscillate, a drive member 309 may also be caused to vibrate or oscillate. The drive member 309 may extend between the proximal end 302 and the distal end 310. The drive member 309 may be an elongate tubular member having a lumen extending therethrough such that material may be aspirated to the console 102 or material may be pumped through the drive member 309 to the distal end 310 of the probe 300.

As depicted in FIG. 3, the distal end 310 of the handpiece housing 301 includes or supports a collar structure 312 that provides a degree of rigidity and support to a vitrectomy needle 320. The vitrectomy needle 320 may include inner and outer components that may be used for cutting vitreous proximate a distal tip 322 of needle 320 during vitrectomy procedures as is described herein and in further detail.

The handpiece housing 301 includes a chamber 330 that extends from the proximal end 302 to the distal end 310. The chamber 330 may be referred to herein as an optical fiber slack chamber 330. A length of an optical fiber 332 extends within the slack chamber 330. For example, the optical fiber 332 may extend from the fiber subsystem 120, through the first conduit 106, through the optical fiber slack chamber 330, through the collar structure 312, and along the vitrectomy needle 320. The fiber may terminate anywhere along the needle 320, such as at or near the distal tip 322 thereof or closer to the distal end 310 of the handpiece housing 301. The optical fiber 332 may be affixed to the needle 320 at a distal region of the fiber 332, which may provide a proximal region of the needle over which the optical fiber 332 is permitted to axially displace independently of the needle 320, in some implementations. In some other implementations (e.g., as seen in FIGS. 4A-6B), the optical fiber 332 may be affixed to the sheath 340. When the needle 320 flexes during use in a medical procedure, the portion of the fiber 332 extending along the needle 320 may relatively, axially displace according to the direction of bending of the needle 320. To prevent strain on the optical fiber 332, the collar structure 312 may include one or more passages with guiding surfaces to permit independent elongate displacement of the optical fiber 332 along a proximal region of the needle 320 within the space between the tubular member 342 and sheath 340, and to permit slideable transition of the optical fiber 332 through a straight, offset or curved path between the needle 320 and the slack chamber 330. The slack chamber 330 may include sufficient space to accommodate slack optical fiber in one or more fiber bends 334. The fiber bends 334 may have a radius of curvature sufficiently large to avoid affecting the illumination passing through the optical fiber 332, while still providing for an amount of slack fiber to be contained within the optical fiber slack chamber 330. The optical fiber 332 may have a portion fixed within the proximal portion of the slack chamber 330 or the distal end of the handpiece housing 301. Accordingly, the amount of slack fiber may accommodate flexing of the vitrectomy needle 320. Some implementations of the probe 300 may include an optical fiber slack chamber in the coupled conduit 106 in addition to or as an alternative to the slack chamber 330 included in the handpiece housing 301.

Figure 4A:
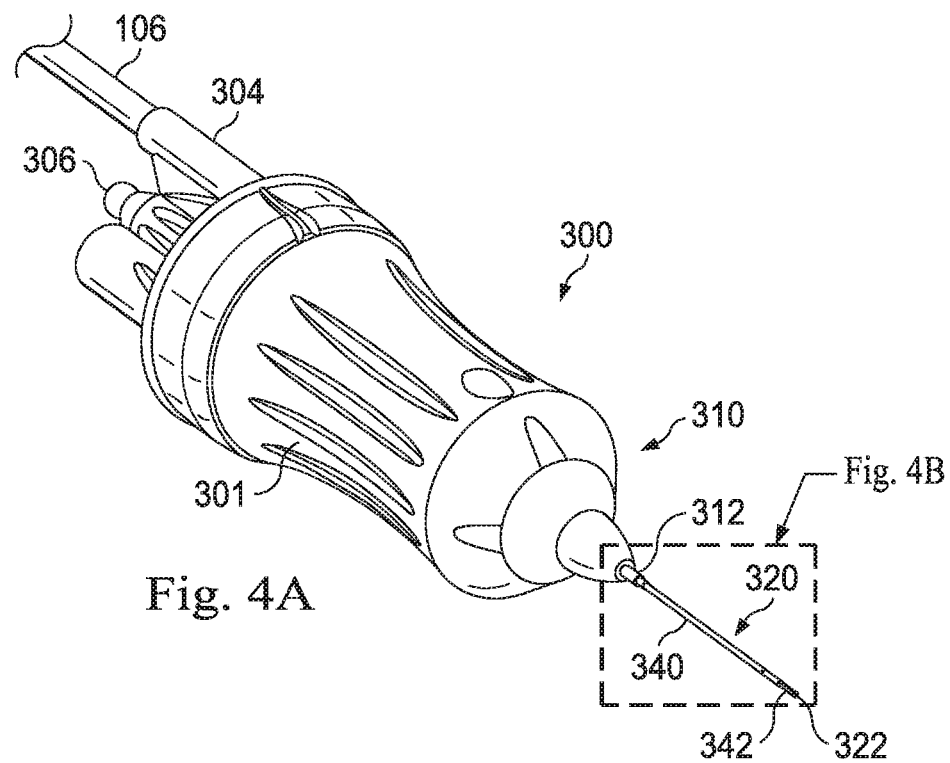
FIG. 4A is a perspective view of the surgical instrument of FIG. 3, according to aspects of the present disclosure.
Figure 4B:
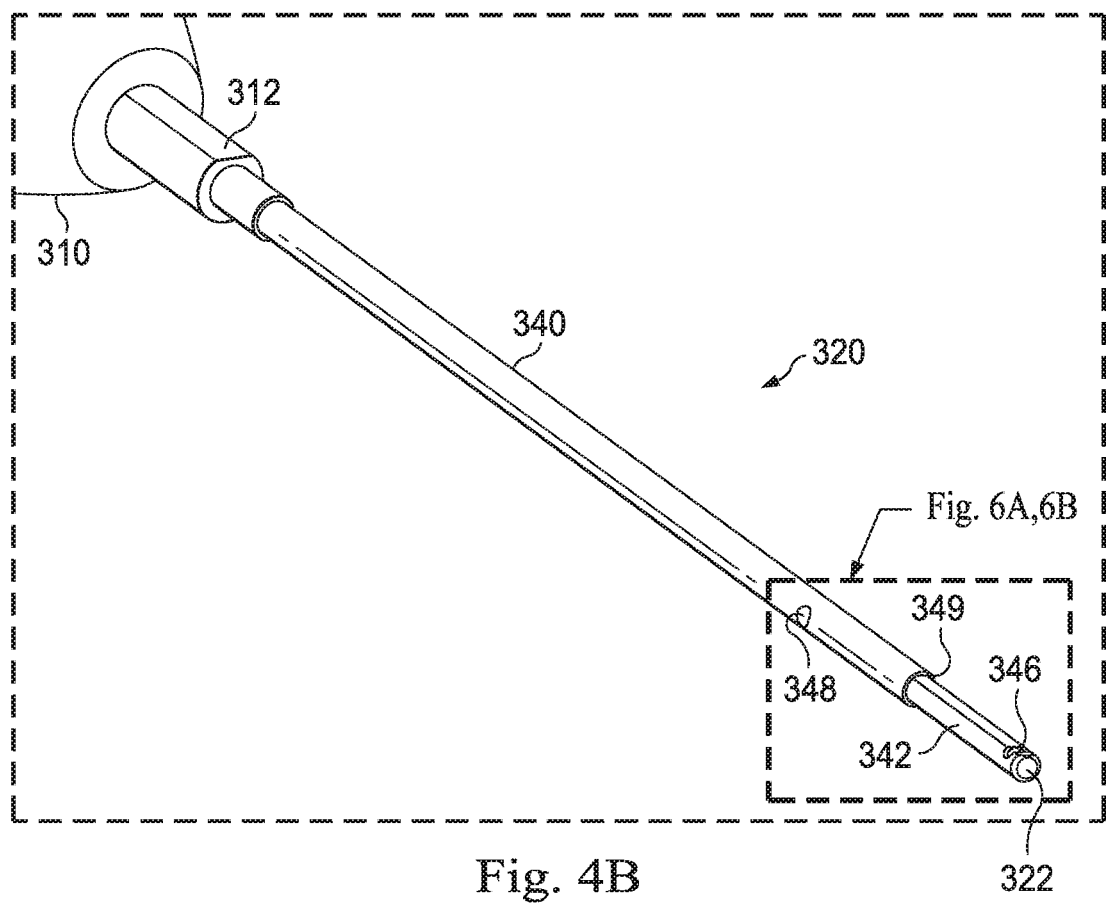
FIG. 4B is a detailed perspective view of a portion of the distal end of the surgical instrument included in FIG. 4A, according to aspects of the present disclosure.

FIGS. 4A and 4B provide perspective views of the probe 300 of FIG. 3. Both of these figures depict an implementation of the needle 320. As shown in FIG. 4A, the needle 320 includes a sheath 340 extending along an outer surface of an elongate tubular member 342. The elongate tubular member 342 extends beyond a distal edge 349 (shown in more detail in FIG. 5A) of the sheath 340. The distal tip 322 may be the distal tip of the elongate tubular member 342. FIG. 4B is a more detailed view of the needle 320 depicted in FIG. 4A. FIG. 4B further illustrates that the elongate tubular member 342 can include an opening or port 346, into which vitreous may be aspirated and cut during a vitrectomy procedure. FIG. 4B also depicts an opening 348 in the sheath 340. The opening 348 may provide a window through which a liquid or gel sealant material may be introduced to seal off any small gaps that are present between the inner surface of the sheath 340 and the outer surface of the elongate tubular member 342. In some implementations, multiple openings may be provided in the sheath 340 to provide for the introduction of a sealant. The opening 348 may also be provided in or proximate to the collar structure 312 at the distal end 310 of the housing 301. In some implementations, the sealant is a gel that can be injected through the opening 348. The gel may be cured after injection to further ensure a proper seal between the sheath 340 and the elongate tubular member 342. Affixing the optical fiber 332 to the sheath 340 may result in passive alignment of the optical fiber 332 relative to the sheath 340. The passive alignment may minimize glare and reduce the assembly cost.

In some implementations, a 360-degree seal may be used between the inner surface of the sheath 340 and the outer surface of the elongate tubular member 342 in order to inhibit potential passage for backflow in the area between the sheath 340 and the tubular member 342. Thus, the liquid or gel sealant material introduced through the opening(s) 348 may extend completely or nearly completely around the circumference of the tubular member 342 to form a seal that extends 360-degrees or nearly 360-degrees around the tubular member 342 between the sheath 340 and tubular member 342. In some implementations, the area between the sheath 340 and tubular member 342 may be partially or fully blocked in other ways, such as by one or more parts, welding, sealant, or any combination thereof.

If the space or gap between the inner surface of the sheath 340 and the outer surface of the elongate tubular member 342 is not adequately closed off or sealed, a possibility exists for a potential passage for backflow in the area between the sheath 340 and the tubular member 342. In a vitreo-retinal procedure, the distal end of the surgical instrument may be placed inside the posterior chamber of the eye, while the proximal end remains outside the patient. Due to the intraocular pressure being higher than atmospheric pressure, there may be a higher pressure at the distal end of the instrument than at the proximal end. If a passage exists in the space or gap between the inner surface of the sheath 340 and the outer surface of the elongate tubular member 342, there is a potential for passive flow of vitreous in that passage due to the higher pressure in the eye as compared to atmospheric pressure. This could lead to traction of the retina or other complications. Accordingly, in some implementations, the area between the sheath 340 and tubular member 342 is partially or wholly closed off as described above, for example by sealant.

Figure 5A:
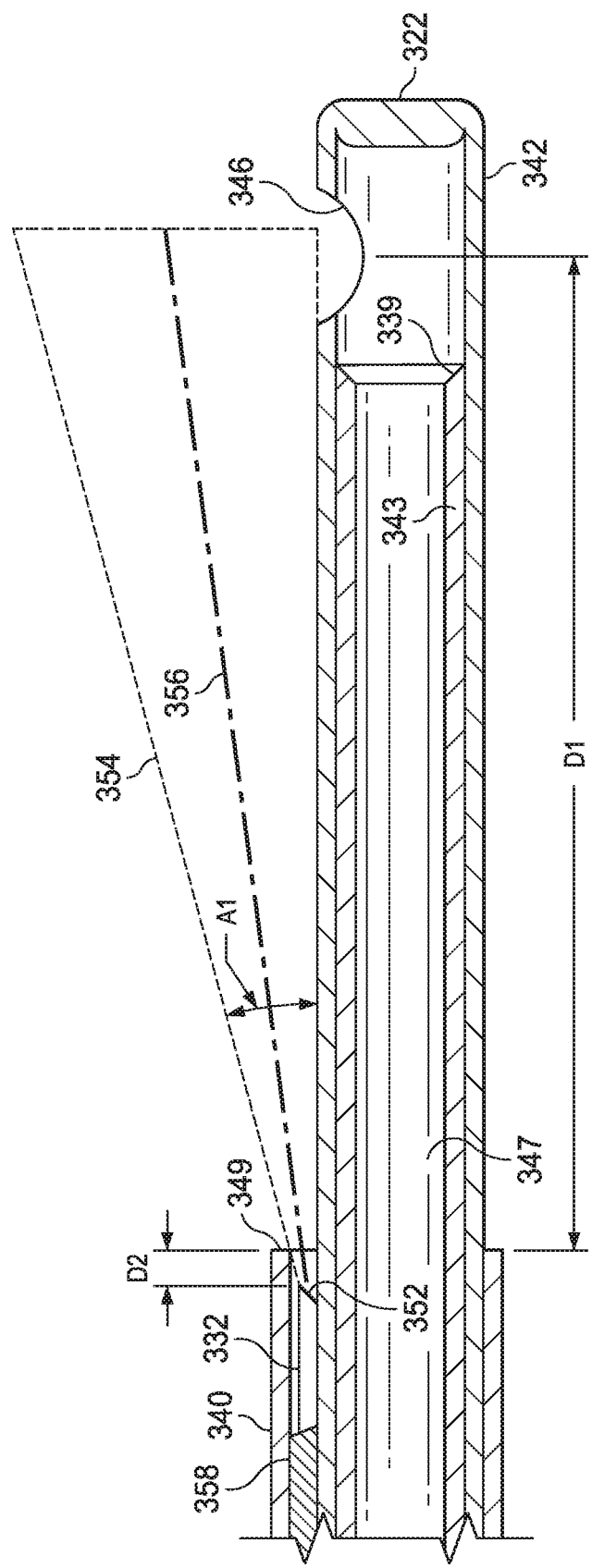
FIG. 5A is a cross-sectional illustration of the distal end of the exemplary surgical instrument in FIG. 3, according to aspects of the present disclosure.

FIG. 5A shows therein a cross-sectional view of the distal region of the vitrectomy needle 320 of FIGS. 3A-C. The sheath 340 surrounds the elongate tubular member 342 and an inner tubular member 343, which is an elongate tubular member extending within a lumen 347 of the elongate tubular member 342. The distal edges 339 of the inner tubular member 343 may be sharpened or include a shape to facilitate cutting of vitreous as the inner tubular member 343 oscillates back and forth within the lumen 347 and cycles past the port 346. Vitreous aspirated into the port 346 may be cut by the oscillating inner tubular member 343.

Figure 5B:
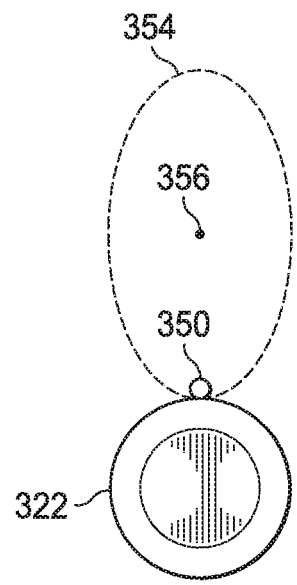
FIG. 5B is an end view of the distal end of the exemplary surgical instrument of FIG. 5A showing an illumination pattern thereof, according to aspects of the present disclosure.
Figure 5C:
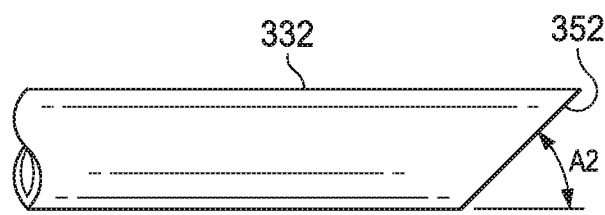
FIG. 5C is a detailed view of a distal end of an optical fiber that may be included in the exemplary surgical instrument of FIG. 5A, according to aspects of the present disclosure.

The sheath 340 further surrounds and encloses the optical fiber 332. A distal edge 349 of the sheath 340 may be offset from a center of the port 346 by a distance D1. The distance D1 may range from about 2 mm to about 3 mm in some implementations. Other implementations may have a distance D1 that is greater or lesser than this range. The optical fiber 332 includes a face 352 at the distal end thereof. Illumination in an illumination beam 354 may be emitted from the face 352 to illuminate an area proximate the port 346. For example, during a vitrectomy procedure, the illumination beam 354 may be generally ovoid in shape and centered at the central illumination point 356, as shown in FIG. 5B. As shown in FIG. 5A, the illumination beam 354 may span an angle A1 and may have a portion that is tangential to the outer surface of the elongate tubular member 342. In some implementations of the probe 300, the face 352 may be angled such that no portion of the illumination beam 354 contacts the outer surface of the elongate tubular member 342 at all. For example, FIG. 5C provides a detailed view of the distal end of the optical fiber 332 and the face 352 thereof. The face 352 may be a beveled face that forms an angle A2, which may range from about 20° to about 50°. In some implementations, the angle A2 is about 35°. Other angles are contemplated in other implementations.

To protect the face 352 at the distal end of the optical fiber 332, the distal end thereof may be offset from the distal edge 349 of the sheath 340 by a distance D2, as shown in FIG. 5A. Implementations of the probe 300 may include a distance D2 ranging from about 10 µm (micrometers) to about 50 µm. In some implementations, the distance D2 may be about 25 µm. This distance D2 may provide sufficient protection of the optical fiber 332 and the face 352 and may also provide a limit to the angle A1 of the illumination beam 354 to control the light and better enable the surgeon to visualize tissue material proximate the distal tip 322, thereby aiding a surgeon in removing vitreous via the port 346. As shown in FIG. 5A, a central illumination point 356 may be angled away from the surface of the outer tubular member 342 to avoid glare being reflected off the exterior surface. In some implementations, some rays of the illumination beam may be incident upon the exterior of the outer tubular member 342.

The gap between the outer surface of the elongate tubular member 342 and the inner surface of the sheath 340 further includes a fill material 358 that covers a portion of the optical fiber 332. The fill material 358 may be an adhesive material that serves to secure the optical fiber 332 to the elongate tubular member 342 and/or the sheath 340. In some implementations, the fill material 358 may be a portion of the sealant material injected through the opening 348 in the sheath 340 as shown in FIG. 4B.

Figure 6A:
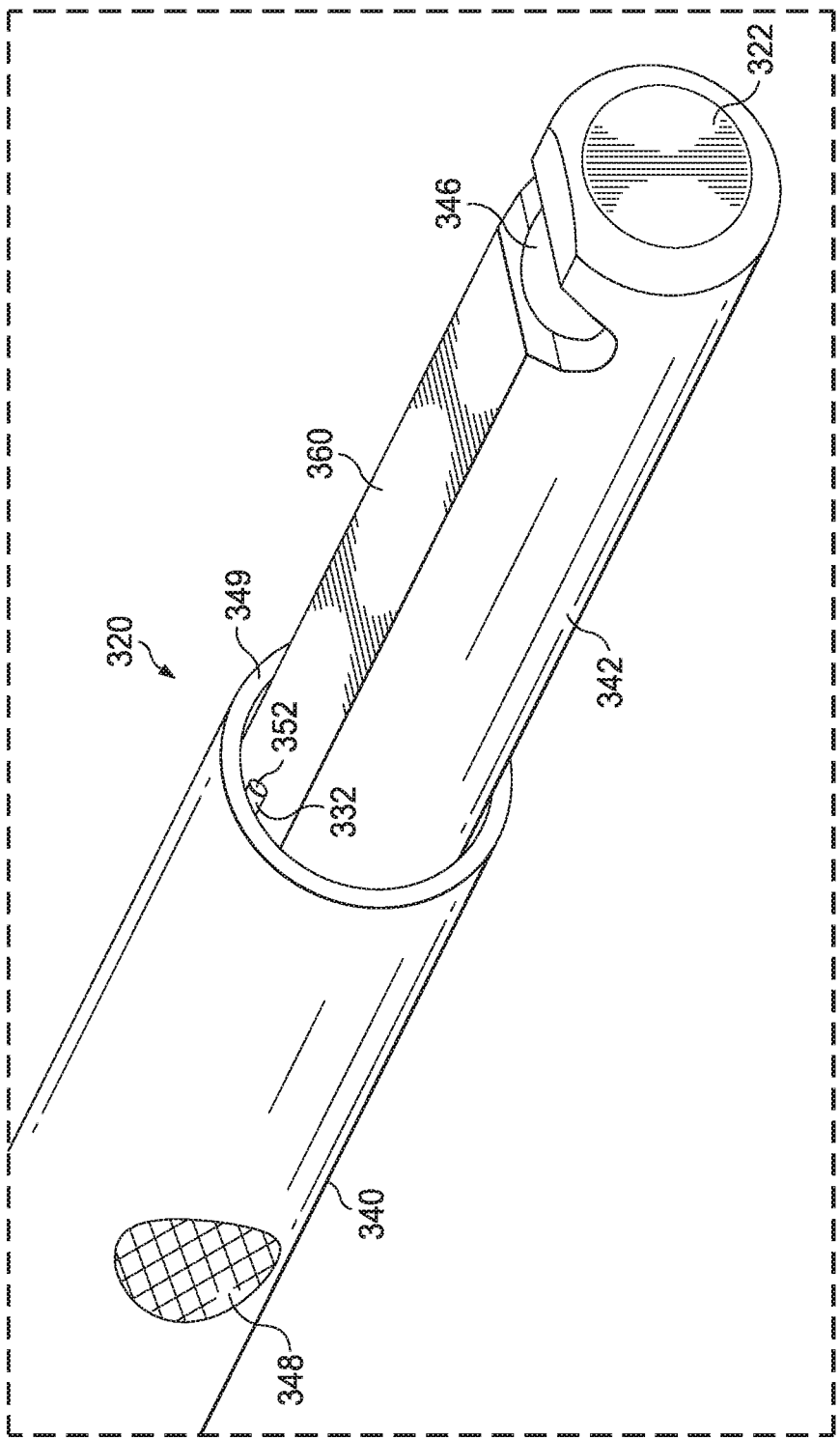
FIGS. 6A and 6B are detailed perspective views of the distal ends of exemplary surgical instruments, according to aspects of the present disclosure.
Figure 6B:
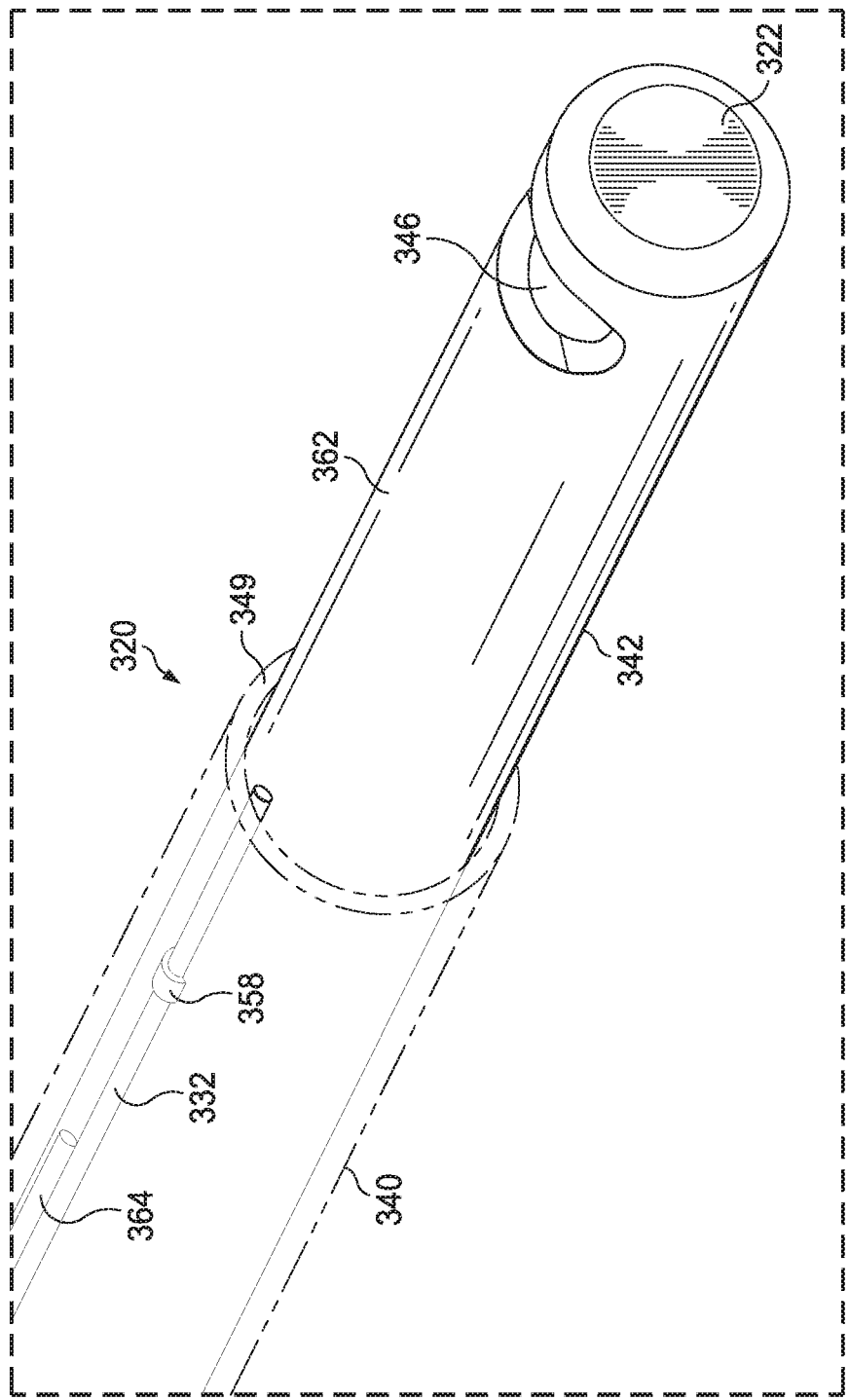

Referring now to FIGS. 6A and 6B, shown therein are implementations of the distal portion of the needle 320 of the probe 300. As shown in FIG. 6A, a sealant material is visible in the opening 348 in the sheath 340. The sealant material may seal off any gaps that would otherwise be present between the elongate tubular member 342 and the sheath 340. FIG. 6A also depicts a flat surface 360 formed on the elongate tubular member 342. The flat surface 360 may provide a surface on which to secure the optical fiber 332. Further the flat surface 360 may be produced by removing material from the elongate tubular member 342 such that the thickness of the wall of the elongate tubular member 342 is smaller at the flat surface 360. This may facilitate inclusion of the optical fiber 332 while mitigating any increase in the diameter of the needle 320. Accordingly, the thickness of the wall removed to provide the flat surface 360 may correspond to the thickness of the optical fiber 332. Thus, in some exemplary implementations for a vitrectomy probe, about 20 µm to about 150 µm of thickness may be removed. In some implementations of the elongate tubular member 342, the lumen 347 extending therethrough may be offset away from the flat surface 360 to provide for a substantially uniform thickness of the wall at the flat surface 360 and of the wall of the elongate tubular member 342 opposite the flat surface 360. The flat surface 360 may be a planar surface, in some implementations.

FIG. 6B depicts an implementation of the needle 320 in which the outer surface of the elongate tubular member 342 is fully cylindrical, i.e. does not include the flat surface 360 shown in FIG. 6A. The implementation shown in FIG. 6B further depicts a patch of the fill material 358 securing the optical fiber 332 in position under the sheath 340. The depicted implementation also shows an elongate structure referred to as a fiber guard member 364, which extends along a length of the elongate tubular member 342. The fiber guard member 364 may prevent a compressive force applied by the sheath 340 from affecting the performance of the optical fiber 332 and may ensure that the optical fiber 332 remains aligned parallel to a central axis of the elongate tubular member 342, and may also ensure that the optical fiber 332 remains free to displace axially along and independently of a proximal region of the elongate tubular member 342, so as to reduce axial strain on the optical fiber 332 while permitting it to move independently into and out of the slack chamber 330. In some implementations, the optical fiber 332 may extend along the fiber guard member 364 for most of the length of the optical fiber 332. The fiber guard member 364 may be an elongate structure, or series of aligned structures, such as a wire made of metal or a polymeric material welded, adhered or otherwise joined to the outer surface of the elongate tubular member 342. Other implementations of the fiber guard member 364 may include a glass fiber or a line of rigidized or cured polymeric material, such as an adhesive. The thickness of the fiber guard member 364 may be greater than a diameter of the optical fiber 332, which may range from about 20 μm to about 150 μm, in various implementations. Accordingly, the thickness of the fiber guard member 364 may range from about 30 μm to about 200 μm, depending on the implementation. Naturally, some implementations of the needle 320 may include both the flat surface 360 and the fiber guard member 364. In some embodiments, a fiber guard member 364 that surrounds the optical fiber 332 may be provided to protect the optical fiber 332. For example, the fiber guard member 364 may be provided by a metallization layer around a length of the optical fiber 332. The metallization layer may provide structural rigidity to the metallized portion of the optical fiber 332. Other rigid polymers may be used rather than metal, in some embodiments. Embodiments of optical fiber 332 having such a protective coating or surrounding structure may have a diameter less than 200 μm or less than 50 μm, for example.

Figure 7A:
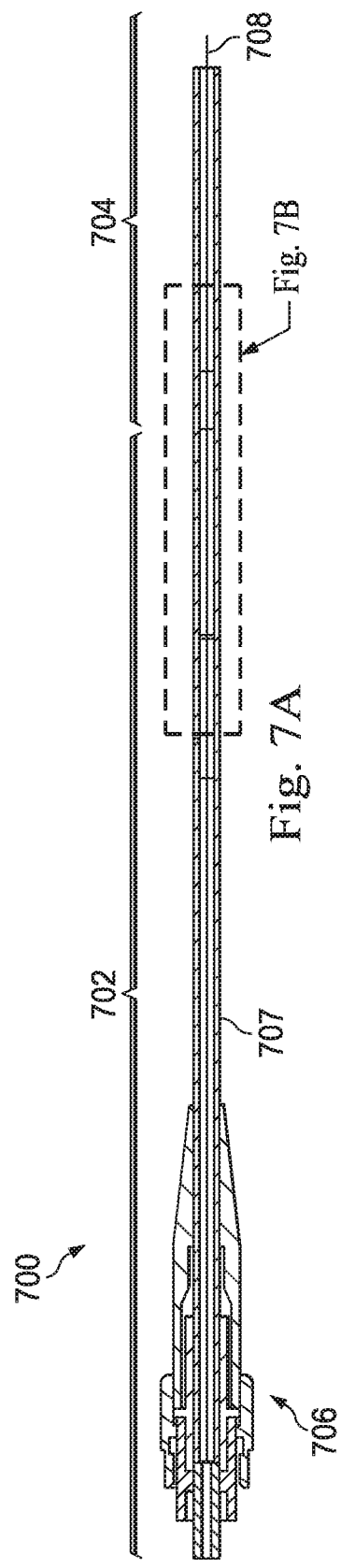
FIGS. 7A, 7B, and 7C depict cross-sectional views of an optical fiber that may be included in exemplary surgical instruments, according to aspects of the present disclosure.
Figure 7B:
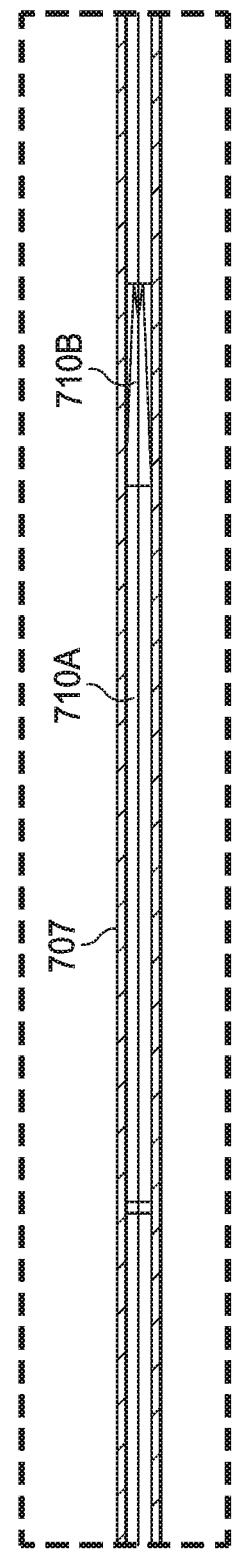
Figure 7C:
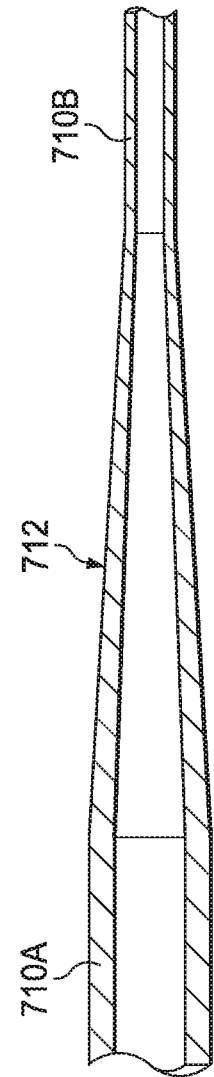

Referring now to FIGS. 7A, 7B, and 7C, shown therein are aspects of an optical fiber 700 which may be used in some implementations of the optical fiber 332. The optical fiber 700 may include a transmission assembly 702 and a distal assembly 704. The transmission assembly 702 may comprise about 80% or 90% of the total length of the optical fiber 700. For example, the transmission assembly 702 may be about 90 inches in length, while the distal assembly 704 may be about 10 inches in length. FIG. 7A depicts an optical fiber coupler 706 disposed at the proximal end of the optical fiber 700. The coupler 706 may secure the optical fiber 700 to the console 102 of FIG. 1 or to the fiber subsystem 120 contained therein. The coupler 706 may include an elongate portion that may prevent kinking close to the proximal end of the optical fiber 700. The optical fiber coupler 706 connects to a flexible outer member 707, which may be the first conduit 106 as shown in FIG. 1 and described herein. Accordingly, the flexible outer member 707 may contain and protect an optical fiber core 708.

FIG. 7B shows the optical fiber core 708 as a compound optical fiber core having multiple components axially aligned and joined to transmit light along the total length thereof. Some implementations of the optical fiber core 708 may include a first fiber portion 710A and a second fiber portion 710B. The fiber portions 710A and 710B may be formed from the same materials or from different materials. For example, the fiber portion 710A may be a silica or borosilicate fiber, while the fiber portion 710B may be a plastic fiber. In other implementations, the fiber portion 710A may be a plastic fiber, while the fiber portion 710B is a glass fiber. The fiber portions 710A and 710B may be glued or fused together.

As shown in FIG. 7C, the fiber portions 710A and 710B may be joined by a tapered optical fiber section 712 that has a proximal end with a first radius and a distal end with the second radius. The tapered optical fiber section 712 may join fiber portions of different diameters. In some implementations, the tapered optical fiber section 712 may be formed by heating the optical fiber core 708 and stretching the fiber. In some implementations, the tapered optical fiber section 712 may be about 20 mm in length, and may join an optical fiber portion 710A having a diameter of about 100 μm with an optical fiber portion 710B having a diameter of about 30 μm. These dimensions are exemplary only, and will vary depending on the implementation. In some implementations, a single, continuous optical fiber core extends the full length of the optical fiber 700.

Figure 8:
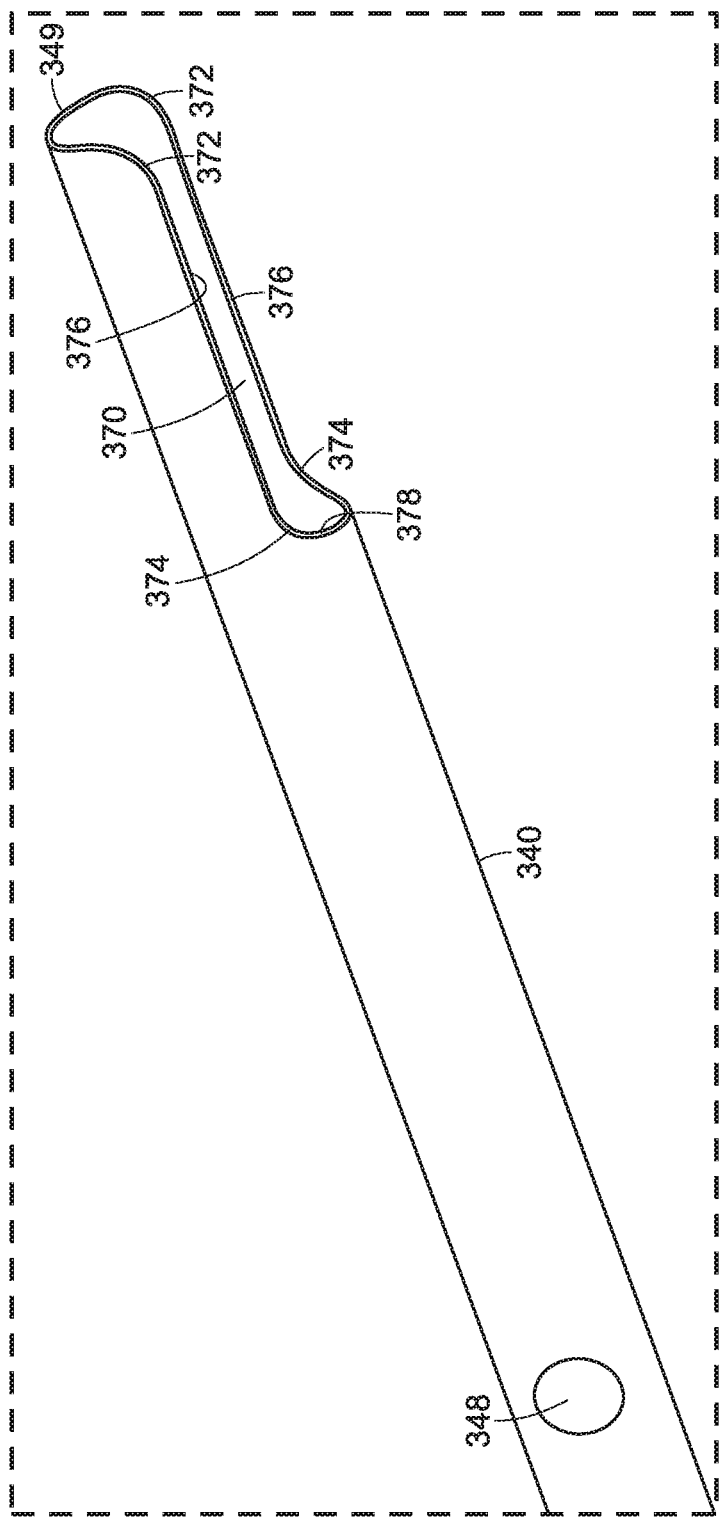
FIG. 8 is a perspective view of an alternative sheath member, according to aspects of the present disclosure.
Figure 9A:
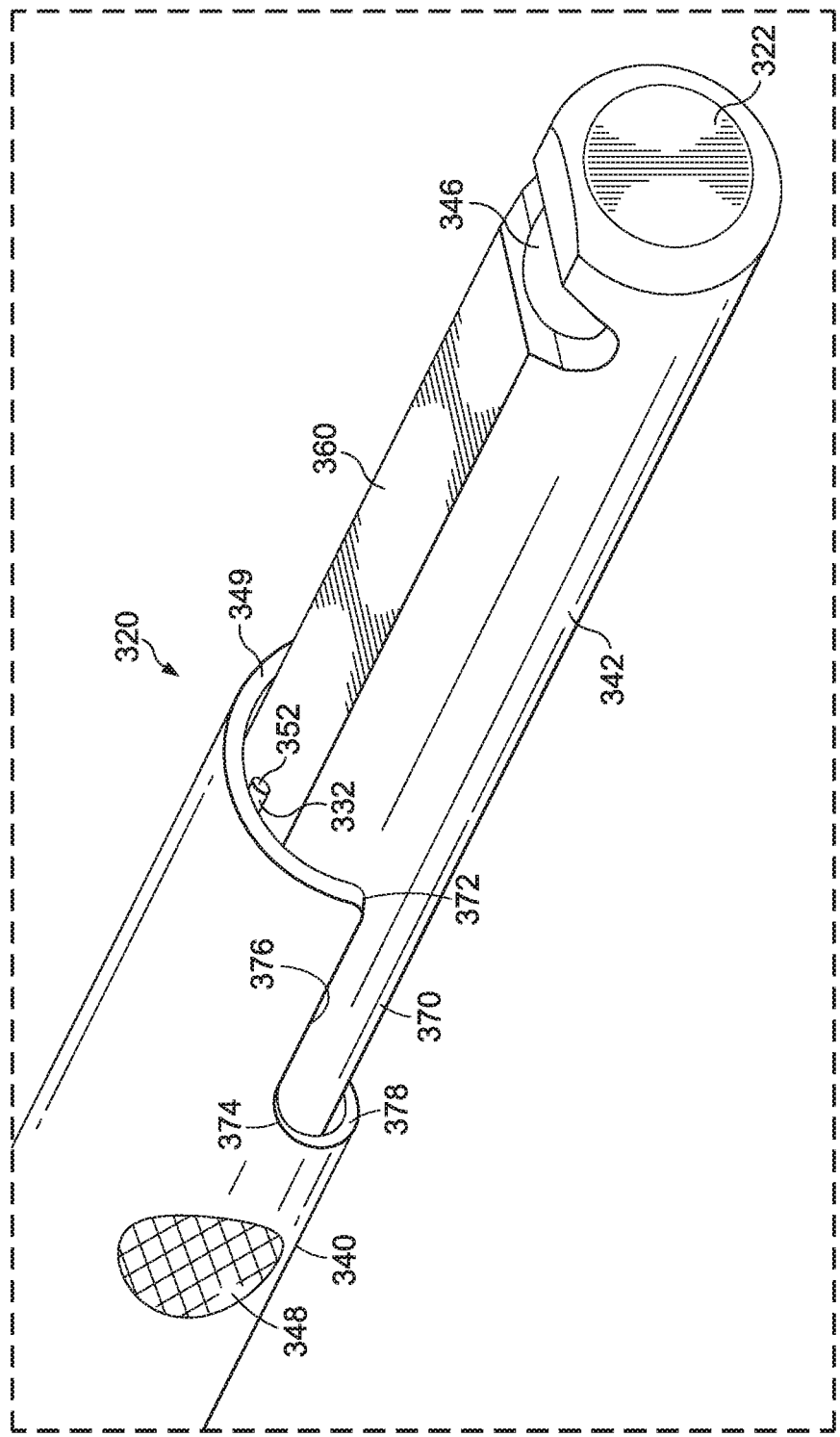
FIGS. 9A and 9B are detailed perspective views of the distal ends of exemplary surgical instruments including the sheath member of FIG. 8, according to aspects of the present disclosure.
Figure 9B:
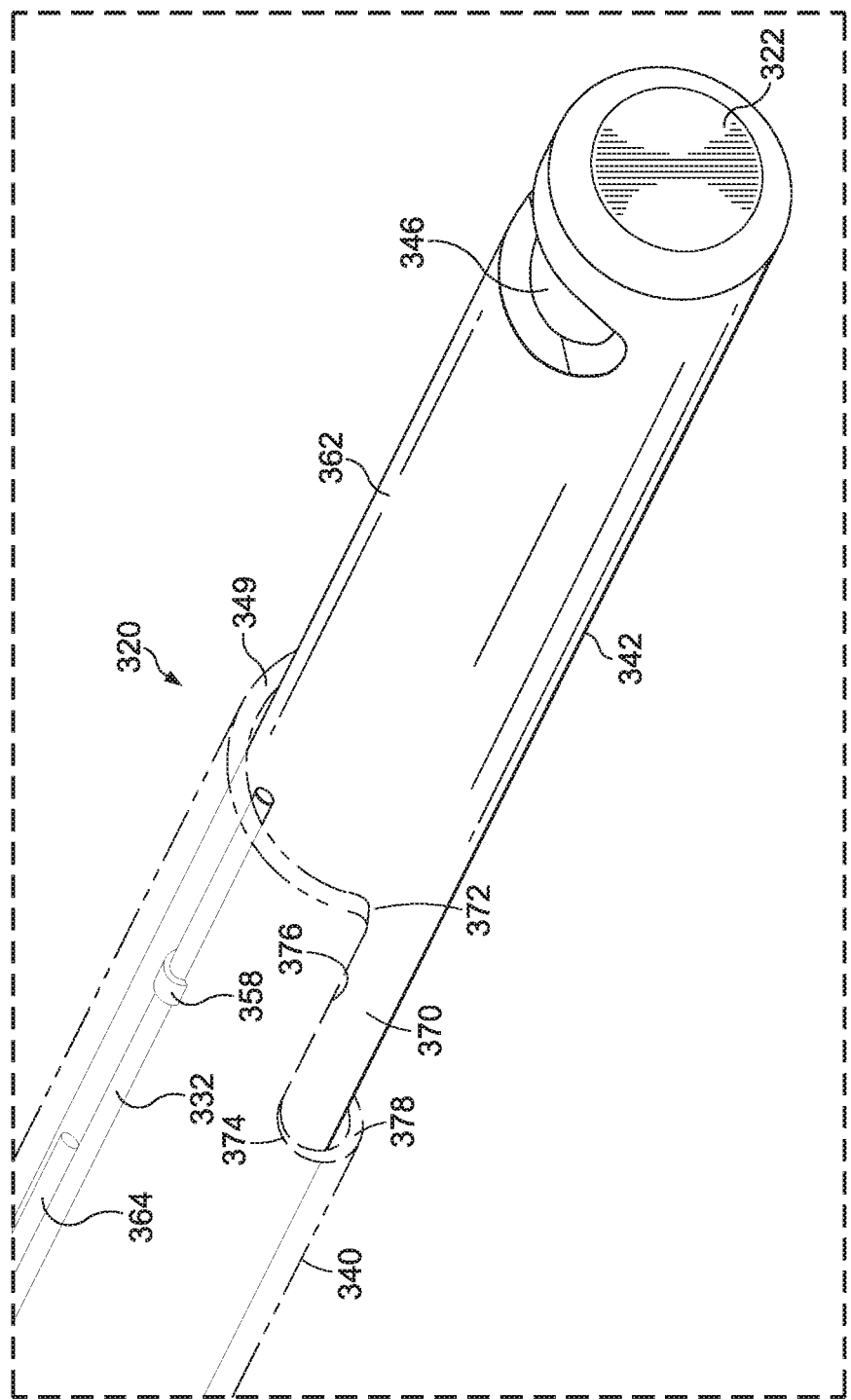

FIG. 8 shows an alternative sheath 340, according to aspects of the present disclosure. FIGS. 9A and 9B show the distal ends of exemplary surgical instruments including the sheath 340 of FIG. 8, according to aspects of the present disclosure.

As described above, with an optical fiber 332 extending along a length of a tubular member 342 between the outer surface of the tubular member 342 and an inner surface of a sheath 340, a space or gap may exist between the tubular member 342 and the sheath 340. In some implementations, the gap between the tubular member 342 and the sheath 340 includes a fill material 358, such as an adhesive material, that covers a portion of the optical fiber 332 and serves to secure the optical fiber 332 to the tubular member 342 and/or the sheath 340. The fill material 358 may be injected through the opening 348 in the sheath 340 as shown in FIG. 4B. The fill material 358 may completely or nearly completely seal the space or gap between the tubular member 342 and the sheath 340 in a circumferential direction around the tubular member 342, for example to prevent passive backflow of vitreous that could otherwise occur due to a higher pressure in the eye as compared to atmospheric pressure.

The fill material 358 may be located proximal to the distal end of the optical fiber 332, so that the fill material 358 does not contaminate or otherwise obstruct the tip of the optical fiber 332. That is, while the fill material 358 may extend around the circumference of the tubular member 342 within the sheath 340, in some implementations the fill material 358 is limited in its extent in the longitudinal direction, and it does not extend to the distal end of the sheath 340. In such a case, distal to the fill material 358, a small unfilled space or gap remains between the tubular member 342 and the sheath 340.

Air may be present in the space or gap between the tubular member 342 and the sheath 340. When the microsurgical instrument or surgical probe is in use, that air may create an air bubble at the distal end of the sheath 340. For example, when the microsurgical instrument or surgical probe is inserted into the human body, such as into the posterior chamber of the eye, the change in temperature from room temperature to body temperature can cause the air within the space or gap between the tubular member 342 and sheath 340 to expand. Because the proximal end of the space or gap may be blocked, such as by the fill material 358 or by other structure, or because of the orientation of the instrument, the expanding air may attempt to escape the space or gap between the tubular member 342 and the sheath 340 by exiting the space or gap at the distal end of the sheath 340. Further, due to surface tension, the escaping air may form an air bubble that remains in place at the distal end of the sheath 340. This, however, is in the location of the distal end of the optical fiber 332, and if an air bubble is created by the exiting air and remains for any period of time at the distal end of the optical fiber 332, the air bubble may interfere with the illumination of the optical fiber 332. This may reduce the illumination and/or result in a suboptimal optical pattern, which may inhibit the visualization benefits of the optical fiber 332.

In order to mitigate or inhibit the formation of air bubbles at the tip of the optical fiber 332, an opening, such as a slot, may be provided in the sidewall of the sheath 340, adjacent to the air gap between the tubular member 342 and the sheath 340, at or near the distal end of the sheath 340, and proximal to the distal edge 349 of the sheath 340. The opening may be located circumferentially away from the tip of the optical fiber 332. Due to the nature of the air expansion in the area between the tubular member 342 and the sheath 340, the air bubble may tend to form at the opening rather than at the tip of the optical fiber 332.

As an example, in FIG. 8, the sheath 340 has an opening 370 in the form of a slot extending proximally from the distal end of the sheath 340, proximal to the distal edge 349 of the sheath 340. The opening or slot 370 is generally positioned circumferentially away from the tip of the optical fiber 332. In the illustrated example (as shown in FIGS. 9A and 9B), the opening or slot 370 is located 180-degrees away from the optical fiber 332, but the opening or slot 370 may be positioned at other locations away from the optical fiber 332. The opening or slot 370 has an edge 376 and a proximal end 378. Where the opening or slot 370 meets the distal edge 349, the corners of the sidewall of the sheath 340 may be rounded such that the sidewall has rounded edges 372, so as to avoid sharp corners, which could cause trauma or injury. Similarly, at the proximal end 378 of the opening or slot 370, the sidewall of the sheath 340 may have rounded edges 374, again to avoid sharp corners.

FIGS. 9A and 9B show the distal ends of surgical instruments that are similar to the surgical instruments shown in FIGS. 6A and 6B, except that in FIGS. 9A and 9B the sheath 340 has an opening or slot 370 as shown in FIG. 8. In such a surgical instrument, when air that is present in the space or gap between the tubular member 342 and the sheath 340 expands, any escaping air bubble(s) will tend to exit that space or gap at the opening or slot 370, away from the distal end of the optical fiber 332. For example, due to the nature of the air expansion, any escaping air bubble(s) will tend to exit that space or gap at the proximal end 378 of the opening or slot 370, or otherwise along the edge 376 of the opening or slot 370, away from the distal end of the optical fiber 332. Thus, the opening or slot 370 directs the air bubble(s) away from the distal end of the optical fiber 332, to mitigate the potential for, or to avoid, having an air bubble interfere with the illumination from the optical fiber 332. In some embodiments, the portion of the tubular member 342 under the slot in the sidewall of the sheath 340 (e.g., the portion of the tubular member adjacent to the air gap at or near the distal end of the sheath 340 and proximal to the distal edge 349 of the sheath 340) may be polished or coated with a low friction coating (or both polished and coated) to further facilitate directing the air bubble(s) away from the distal end of the optical fiber 332.

Figure 10:
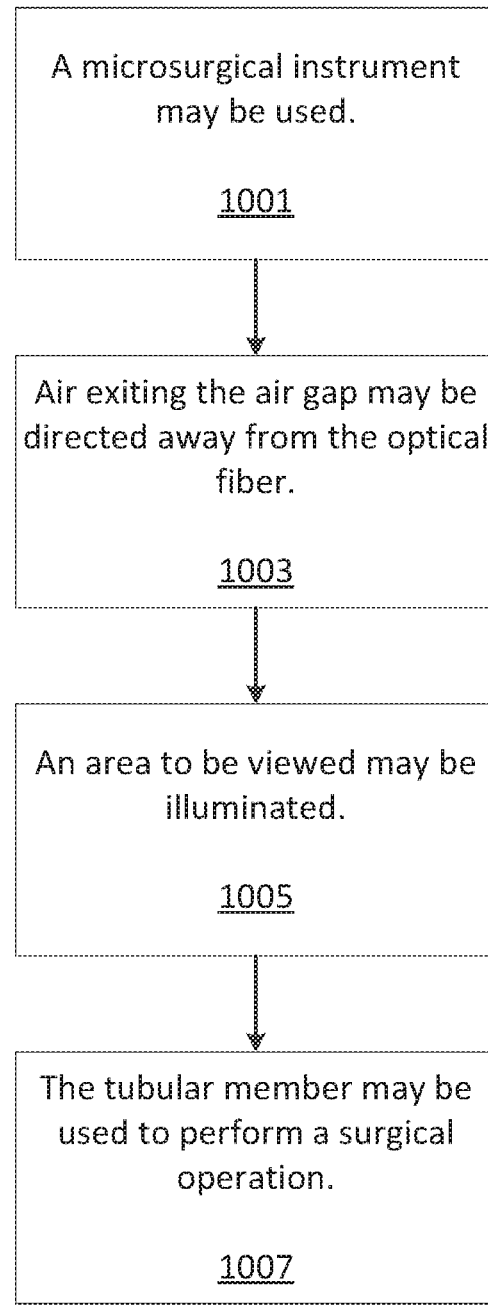
FIG. 10 illustrates a method of using a microsurgical instrument with a sheath, according to an embodiment.

FIG. 10 illustrates a method of using a microsurgical instrument with a sheath, according to an embodiment. The elements provided in the flowchart are illustrative only. Various provided elements may be omitted, additional elements may be added, and/or various elements may be performed in a different order than provided below.

At 1001, a microsurgical instrument may be used. In some embodiments, the microsurgical instrument may include a tubular member having a distal tip and an outer surface. The instrument may further include a sheath member surrounding a portion of the tubular member and extending toward the distal tip of the tubular member and an optical fiber extending along a length of the outer surface of the tubular member between the tubular member and the sheath member. A tip of the optical fiber may be directed toward the distal tip of the tubular member. The sheath member may include an opening in a sidewall of the sheath member located adjacent to an air gap between the tubular member and the sheath member, proximal to a distal edge of the sheath member, and circumferentially away from the tip of the optical fiber.

At 1003, air exiting the air gap may be directed away from the optical fiber. The opening in the sidewall of the sheath member may be configured to direct air away from the optical fiber.

At 1005, an area to be viewed may be illuminated during the medical procedure by directing light from the tip of the optical fiber.

At 1007, the tubular member may be used to perform a surgical operation in the area being illuminated by light from the optical fiber.

As noted herein, some of the more specific implementations are described with respect to a vitrectomy probe in which an optical fiber provides for illumination of the vitreous at the distal tip of the vitrectomy probe. It should be noted that the described optical fiber may provide for other functions in other implementations. For example, the optical fiber included in implementations of the surgical instrument 110 may provide for transmission of laser light to provide a photocoagulation laser at a distal tip of the surgical instrument. Additionally, the surgical instrument 110 may be a non-surgical medical instrument in other implementations. For example, additional implementations may utilize the optical fiber in the performance of optical coherence tomography (OCT) imaging, rather than or in addition to any surgical functions performed by implementations of the medical instrument. Accordingly, such surgical instruments are included within the scope of the present disclosure.

Persons of ordinary skill in the art will appreciate that the implementations encompassed by the present disclosure are not limited to the particular exemplary implementations described above. In that regard, although illustrative implementations have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An illuminated microsurgical instrument system comprising:
a microsurgical instrument having a distally projecting tubular member arranged to perform a medical procedure at an interventional site, the tubular member having a distal tip and an outer surface;
a sheath member surrounding a portion of the tubular member and extending toward the distal tip of the tubular member; and
an optical fiber extending along a length of the outer surface of the tubular member between the tubular member and the sheath member, wherein at least a portion of the outer surface of the tubular member and at least a portion of an inner surface of the sheath member are sealed together such that the tubular member and sheath member are fixed relative to each other;
wherein a tip of the optical fiber is directed toward the distal tip of the tubular member;
wherein the sheath member further comprises an opening in a sidewall of the sheath member, the opening being located adjacent to an air gap between the tubular member and the sheath member, proximal to a distal edge of the sheath member, and circumferentially away from the tip of the optical fiber, wherein the opening is adapted to direct air exiting the air gap away from the optical fiber.

2. The illuminated microsurgical instrument system of claim 1, wherein the opening is a slot located approximately 180-degrees away from the optical fiber.

3. The illuminated microsurgical instrument system of claim 1, wherein corners of the sidewall of the sheath has rounded edges where the opening meets the distal edge of the sidewall and wherein the sidewall of the sheath has rounded edges at a proximal end of the opening.

4. The illuminated microsurgical instrument system of claim 1, wherein the outer surface of the tubular member includes a flat surface, and wherein the optical fiber extends along a length of the flat surface.

5. The illuminated microsurgical instrument system of claim 1, wherein the distal edge of the sheath member is disposed at a location closer to the distal tip of the tubular member than is the optical fiber, such that the optical fiber is recessed from the distal edge.

6. The illuminated microsurgical instrument system of claim 1, wherein the tip of the optical fiber is beveled at an angle toward the outer surface of the tubular member.

7. The illuminated microsurgical instrument system of claim 6, wherein the tip of the optical fiber causes a field of illumination to be directed substantially away from the outer surface of the tubular member.

8. The illuminated microsurgical instrument system of claim 6, wherein a face of the optical fiber forms an angle with respect to the outer surface of the tubular member ranging from about 30 degrees to about 40 degrees.

9. The illuminated microsurgical instrument system of claim 8, further comprising a fiber guard member disposed along a length of the microsurgical instrument adjacent to the optical fiber, to protect the optical fiber from compressive forces between the outer surface of the tubular member and the sheath member.

10. The illuminated microsurgical instrument system of claim 9, wherein the fiber guard member is a rigid structural member surrounding a length of the optical fiber.

11. The illuminate microsurgical instrument system of claim 9, wherein the fiber guard member is a metal wire, a glass fiber, or a line formed of rigidized polymeric material.

12. The illuminated microsurgical instrument system of claim 1, further comprising an opening extending through a sidewall of the sheath member, the opening providing access to a volume defined by and between an inner wall of the sheath member and the outer surface of the tubular member, and wherein cured adhesive at least partially fills the volume defined by and between the inner wall of the sheath member and the outer surface of the tubular member to provide the seal therebetween.

13. The illuminated microsurgical instrument system of claim 12, wherein the opening is in the form of a slot extending proximally from the distal edge of the sheath member.

14. The illuminated microsurgical instrument system of claim 1, wherein the optical fiber comprises a proximal portion having a first diameter and a distal portion have a second diameter that is smaller than the first diameter.

15. An illuminated medical probe comprising:
a handpiece housing configured to be held in a human hand, the handpiece housing including:
a proximal end arranged to receive an optical fiber coupled to an illumination source,
a distal end coupled by a collar structure to an elongate tubular member, and
an optical fiber slack chamber disposed between the proximal end and the distal end; and
an optical fiber extending within the optical fiber slack chamber and extending through the collar structure and along a portion of the elongate tubular member, wherein a distal region of the optical fiber is secured at a distal end thereof to the elongate tubular member, the optical fiber being arranged to axially displace along the elongate tubular member and slideably transition through the collar structure between the elongate tubular member and a slack portion including one or more bends disposed within the optical fiber slack chamber;
wherein at least a portion of an outer surface of the tubular member and at least a portion of an inner surface of the sheath member are sealed together such that the tubular member and sheath member are fixed relative to each other;
wherein the sheath member further comprises an opening in a sidewall of the sheath member, the opening being located adjacent to an air gap between the tubular member and the sheath member, proximal to a distal edge of the sheath member, and circumferentially away from the tip of the optical fiber, wherein the opening is adapted to direct air exiting the air gap away from the optical fiber.

16. The illuminated medical probe of claim 15, wherein the opening is a slot located approximately 180-degrees away from the optical fiber.

17. The illuminated medical probe of claim 15, wherein corners of the sidewall of the sheath has rounded edges where the opening meets the distal edge of the sidewall and wherein the sidewall of the sheath has rounded edges at a proximal end of the opening.

18. The illuminated medical probe of claim 15, wherein the optical fiber slack chamber is disposed in the handpiece housing, or in a flexible conduit coupled to the handpiece housing, or in an optical connector.

19. The illuminated medical probe of claim 15, wherein the optical fiber includes a tapered optical fiber section coupling a proximal fiber section having a first diameter to a distal fiber section having a second diameter that is smaller than the first diameter.

20. A method of performing a medical procedure using an illuminated microsurgical instrument system, the method comprising:
using a microsurgical instrument comprising a tubular member, the tubular member having a distal tip and an outer surface, a sheath member surrounding a portion of the tubular member and extending toward the distal tip of the tubular member, and an optical fiber extending along a length of the outer surface of the tubular member between the tubular member and the sheath member, wherein a tip of the optical fiber is directed toward the distal tip of the tubular member, wherein the sheath member further comprises an opening in a sidewall of the sheath member, the opening being located adjacent to an air gap between the tubular member and the sheath member, proximal to a distal edge of the sheath member, and circumferentially away from the tip of the optical fiber, wherein at least a portion of the outer surface of the tubular member and at least a portion of an inner surface of the sheath member are sealed together such that the tubular member and sheath member are fixed relative to each other;

directing air exiting the air gap away from the optical fiber, wherein the opening in the sidewall of the sheath member is configured to direct air away from the optical fiber;

illuminating an area to be viewed during the medical procedure by directing light from the tip of the optical fiber; and using the tubular member to perform a surgical operation in the area being illuminated by light from the optical fiber.

\* \* \* \* \*